US012679846B2

(12) United States Patent
Shin et al.

(10) Patent No.: US 12,679,846 B2
(45) Date of Patent: Jul. 14, 2026

(54) XANTHONE COMPOUND HAVING EXCELLENT ANTICANCER EFFECT

(71) Applicant: KOREA INSTITUTE OF OCEAN SCIENCE & TECHNOLOGY, Busan (KR)

(72) Inventors: Hee Jae Shin, Busan (KR); Byeoung Kyu Choi, Chungcheongnam-do (KR); Hwa Sun Lee, Busan (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 207 days.

(21) Appl. No.: 18/565,799

(22) PCT Filed: Dec. 9, 2021

(86) PCT No.: PCT/KR2021/018573
§ 371 (c)(1),
(2) Date: Nov. 30, 2023

(87) PCT Pub. No.: WO2023/106452
PCT Pub. Date: Jun. 15, 2023

(65) Prior Publication Data

US 2024/0158411 A1 May 16, 2024

(30) Foreign Application Priority Data

Dec. 7, 2021 (KR) ........................ 10-2021-0173763

(51) Int. Cl.
*C07D 493/04* (2006.01)
*A61K 31/366* (2006.01)
*A61P 35/00* (2006.01)

(52) U.S. Cl.
CPC ............ *C07D 493/04* (2013.01); *A61P 35/00* (2018.01); *C07B 2200/07* (2013.01)

(58) Field of Classification Search
CPC ...... C07D 493/04; A61K 31/366; A61P 35/00
USPC .......................................... 549/275; 514/453
See application file for complete search history.

(56) References Cited

U.S. PATENT DOCUMENTS 5,270,182 A 12/1993 Franco et al.

FOREIGN PATENT DOCUMENTS

| | | | |
|---|---|---|---|
| CN | 108558899 | A | 9/2018 |
| JP | H0725893 | A | 1/1995 |
| KR | 1020150122946 | A | 8/2016 |
| KR | 1020200001861 | A | 5/2020 |

OTHER PUBLICATIONS

Sangwan, K. et al.: Pharmacological aspects of FDA-approved novel drug therapies against cancer in 2023, a comprehensive review. Naunyn Schmiedberg. Arch. Pharmacol., vol. 398, pp. 9737-9766, 2025.*

Chen, Kuanwei, et al. "Calixanthomycin A: Asymmetric Total Synthesis and Structural Determination." Organic Letters 23.5 (2021): 1769-1774.

Kang, Hahk-Soo, and Sean F. Brady. "Mining soil metagenomes to better understand the evolution of natural product structural diversity: pentangular polyphenols as a case study." Journal of the American Chemical Society 136.52 (2014): 18111-18119.

* cited by examiner

*Primary Examiner* — Charanjit Aulakh
(74) *Attorney, Agent, or Firm* — CANTOR COLBURN LLP

(57) ABSTRACT

The present invention relates to a novel xanthone compound, an optical isomer thereof or a pharmaceutically acceptable salt thereof that exhibits cytotoxicity against cancer cell lines and inhibits cancer cell growth, thereby exhibiting excellent preventive or therapeutic effects on various cancer cells.

6 Claims, 6 Drawing Sheets

【FIG. 1】
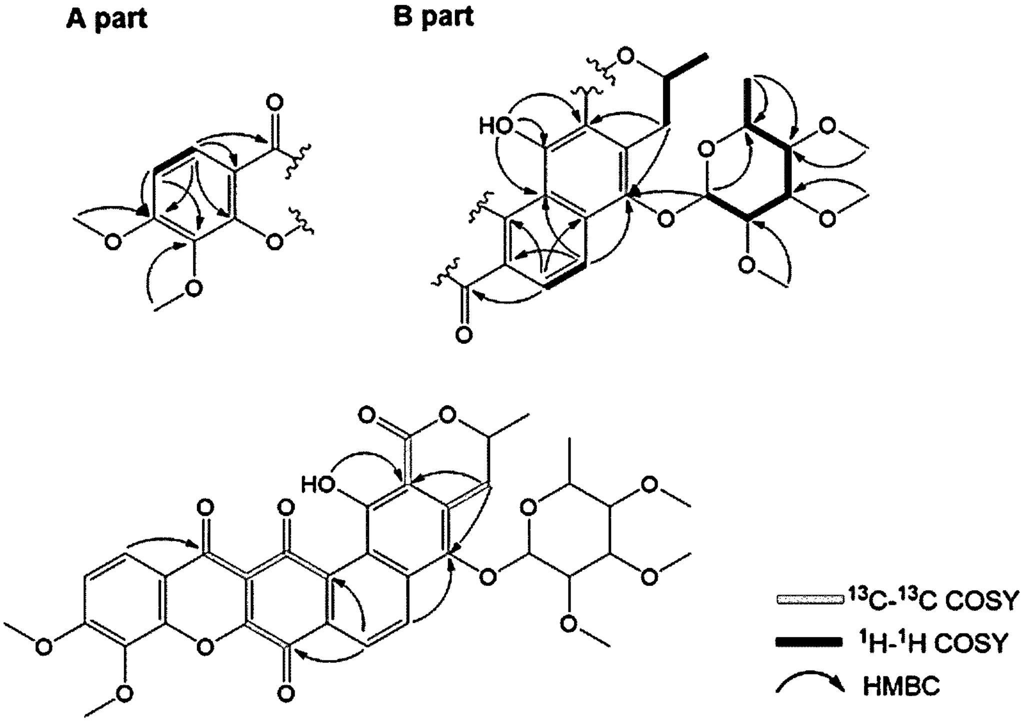

【FIG. 2】
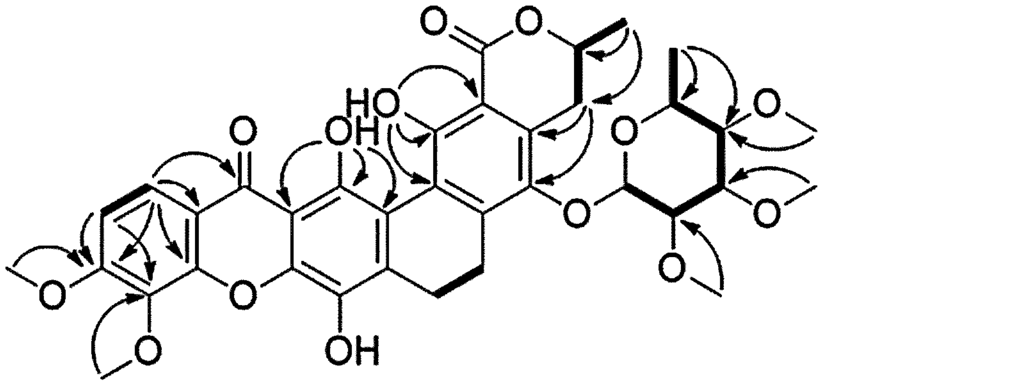

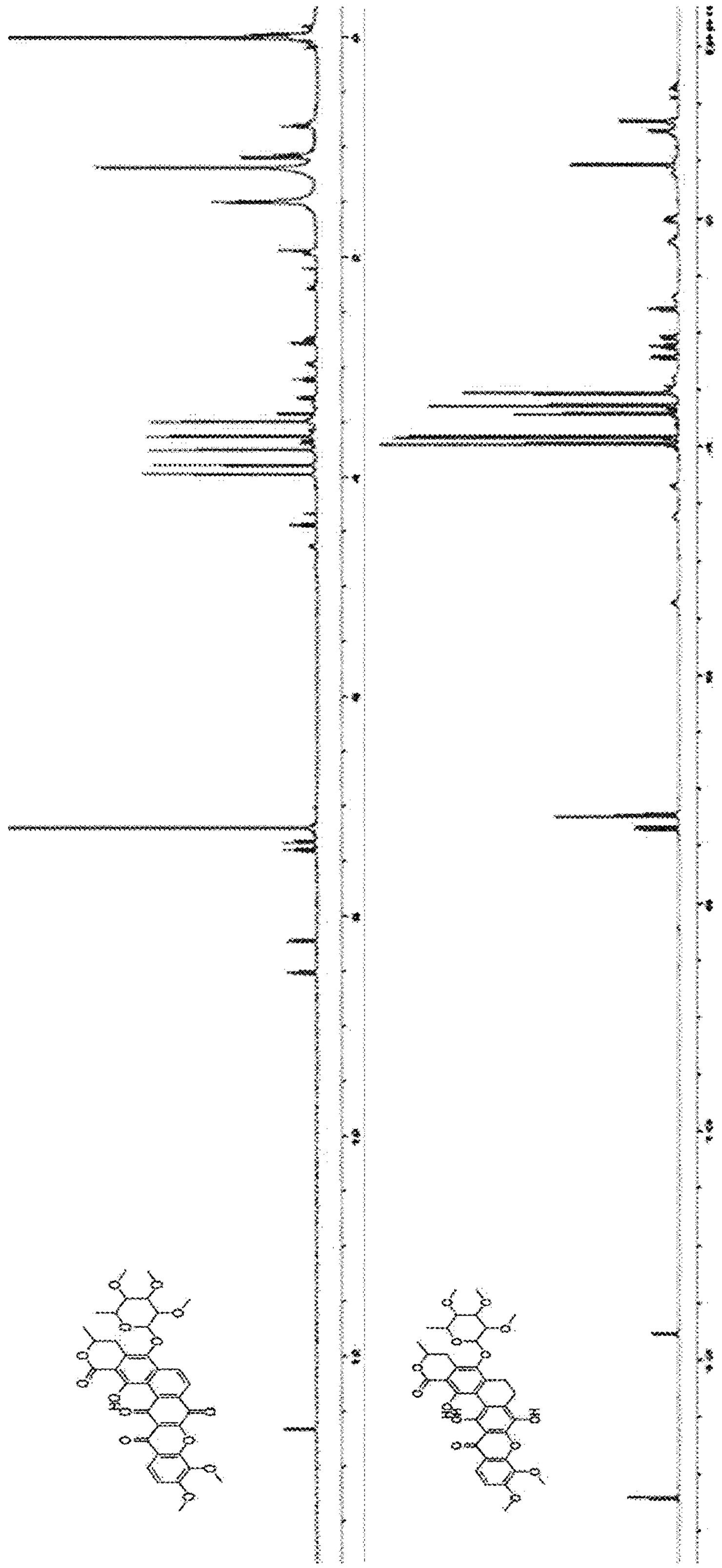
[FIG. 3]

【FIG. 4】
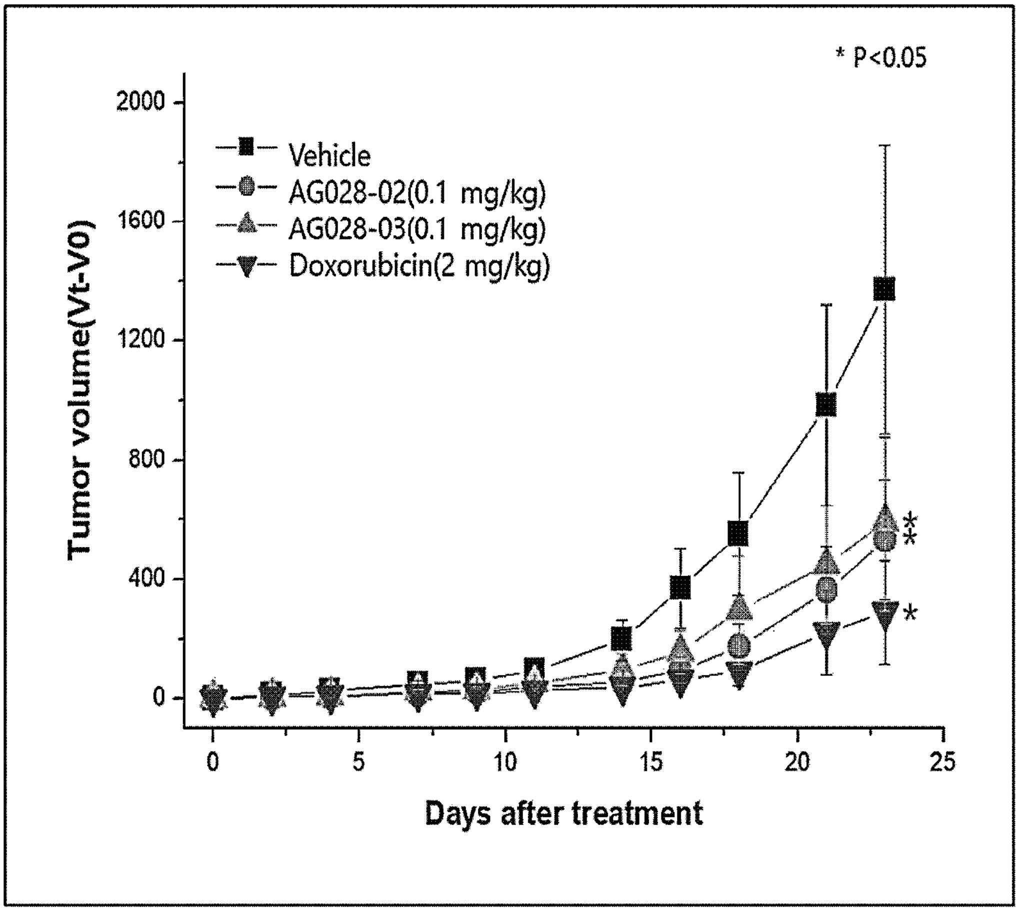

【FIG. 5】
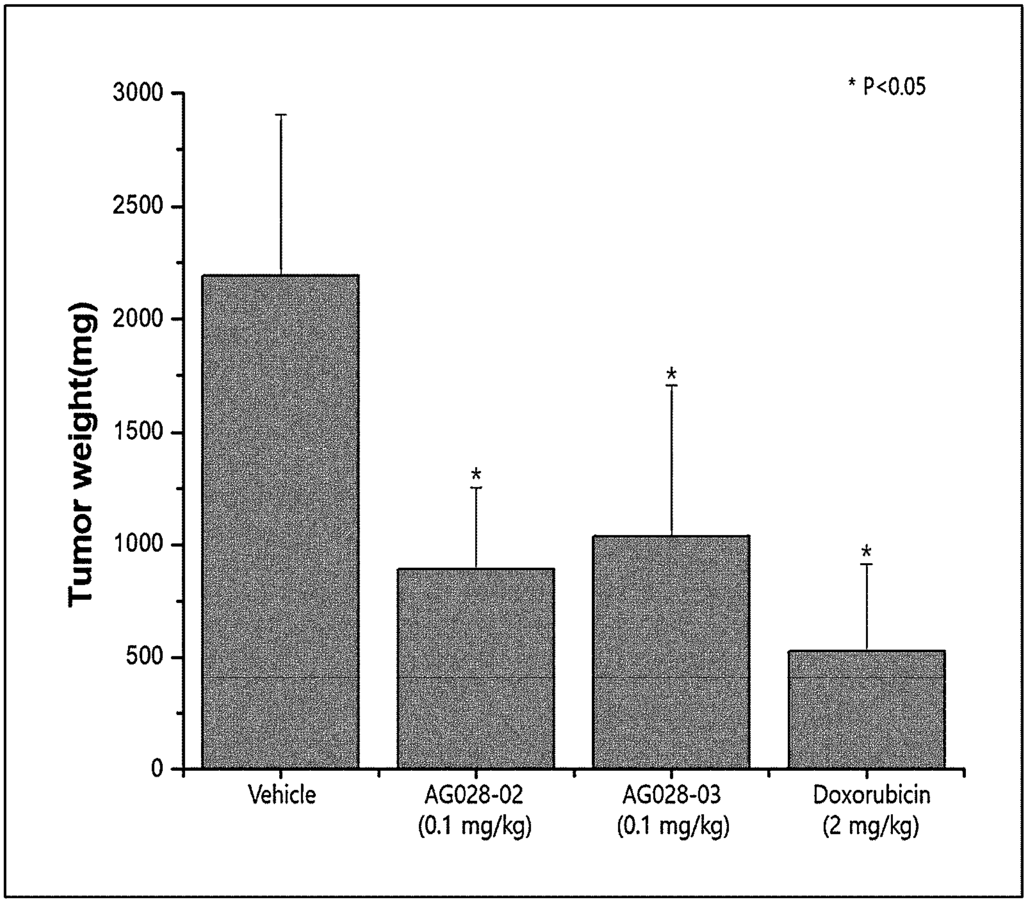

【FIG. 6】
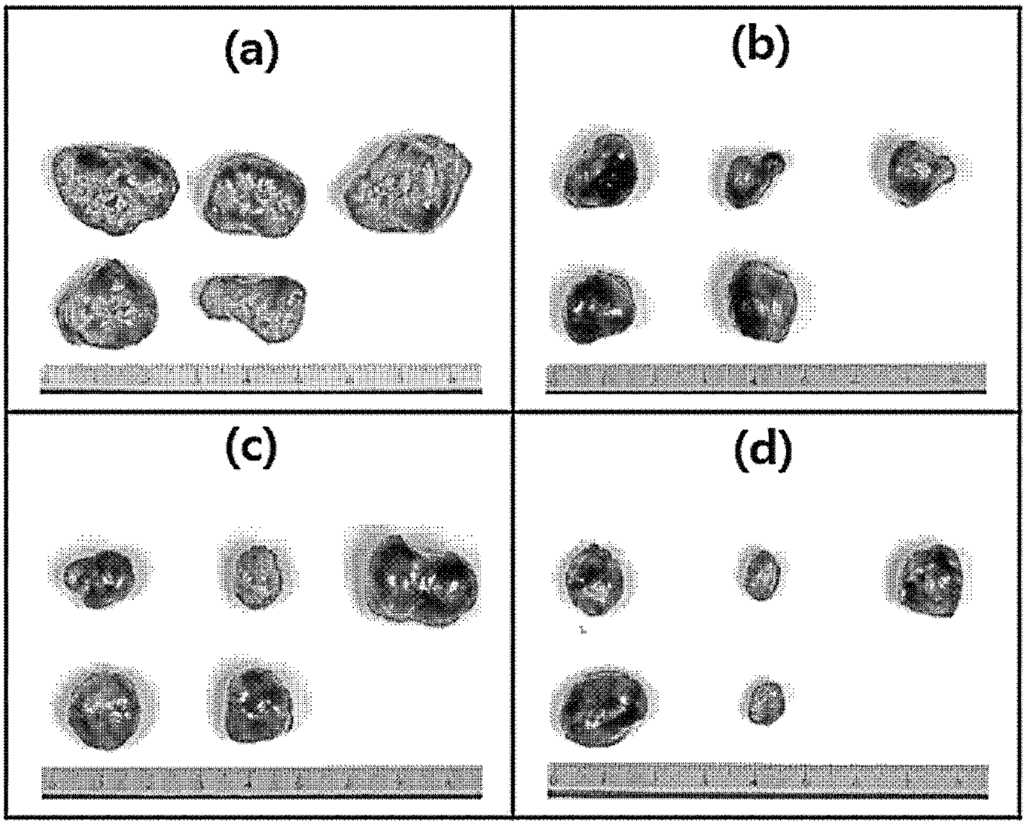

XANTHONE COMPOUND HAVING EXCELLENT ANTICANCER EFFECT

CROSS REFERENCE TO RELATED APPLICATIONS

This application is a US National Stage application of PCT/KR2021/018573, filed Dec. 9, 2021, which claims the benefit of Korean Patent Application No. 10-2021-0173763 filed on Dec. 7, 2021, both of which are incorporated by reference in their entirety herein.

TECHNICAL FIELD

The present invention relates to a novel xanthone compound having an excellent anticancer effect.

BACKGROUND ART

Xanthones are known to be secondary metabolites produced by some terrestrial (flora, fungi and lichen) or marine microorganisms. Xanthone was first isolated in 1855 by a German scientist studying dysentery, and was later named xanthos, which means yellow in Greek. Xanthone has unique 9H-Xanthen-9-one, which is related to the structure of flavonoids. While flavonoids are frequently found in nature, xanthones are rarely found and are mainly found in plants of the Gentiaceae and Hispicae families and some fungi and lichens. Several types of xanthones have been identified, including simply oxygenated xanthones, xanthone glycosides, prenylated xanthones, xanthonolinoids, and others. Research on xanthones has received a lot of attention because of not only structural diversity but also various pharmacological effects. Among them, polycyclic xanthones isolated from actinomycetes are known to exhibit strong cytotoxicity and antibacterial activity. In addition, various studies on the structure, biological activity, biosynthesis, and chemical derivatization of polycyclic xanthones have been reported.

In this regard, in Korean Patent Publication No. 10-2015-0122946, there are disclosed novel xanthone compounds, such as 1-hydroxy-7-methoxy-2,8-bis(3-methylbut-2-en-1-yl)-9-oxo-9H-xanthene-3,6-diyl acetate; 6,8-dihydroxy-2-methoxy-1,7-bis(3-methylbut-2-en-1-yl)-9-oxo-9H-xanthene-3-ylacetate; 3-(allyloxy)-6,8-dihydroxy-2-methoxy-1,7-bis(3-methylbut-2-en-1-yl)-9H-xanthen-9-one; 3,6-dihydroxy-1,7-dimethoxy-2,8-bis(3-methylbut-2-en-1-yl)-9H-xanthen-9-one; 3-amino-8-hydroxy-1,7-diisopentyl-2-methoxy-9H-xanthen-9-one; 1,3,6,7-tetrahydroxy-2,8-diisopentyl-4-nitro-9H-xanthene-9-one; or 4-chloro-1,3,6-trihydroxy-2,8-diisopentyl-7-methoxy-9H-xanthen-9-one.

In addition, in Korean Patent Registration No. 10-2020-0001861, there is disclosed a novel xanthone compound having a specific Chemical Formula.

Marine environment has served as an important reservoir of natural products for new drugs over the past decades. In particular, marine microorganisms are considered efficient producers of lead compounds with biomedical potential. In addition, structurally diverse and notable biologically active natural products have been identified from marine microorganisms.

Dokdo in the East Sea of Korea is an island consisting of 89 small islets and rocks, and unlike the inland Korean Peninsula, a sea area directly affected by the complex ocean currents of the Tsushima Warm Current and the North Korean Cold Current. The sea area near Dokdo is a habitat where a variety of temperate and subtropical species may inhabit. Due to these characteristics, the marine biological resources of Dokdo have potential value and are known to exhibit high biological diversity relative to its area. The present inventors isolated a strain *Actinomadura gelibolu-ensis* 188DD-028 (Strain Accession Number: KCTC 14764BP) from unidentified sponge samples collected through scuba diving in the coastal waters of Dokdo. Subsequently, the present inventors identified two novel xanthone compounds based on the results of fermentation, solvent extraction, and chemical analysis of the producing strain, confirmed the cytotoxicity of the novel xanthones against various cancer cell lines, and then completed the present invention.

DISCLOSURE

Technical Problem

An object of the present invention is to provide at least one selected from the group consisting of novel xanthone compounds having excellent anticancer effects against various cancer cells, an optical isomer thereof, and a pharmaceutically acceptable salt thereof.

Another object of the present invention is to provide a method for preparing the novel xanthone compound, an optical isomer thereof, and a pharmaceutically acceptable salt thereof.

Yet another object of the present invention is to provide a pharmaceutical composition having excellent anticancer prevention or treatment effects.

Yet another object of the present invention is to provide a food composition having excellent anticancer prevention or improvement effects.

Yet another object of the present invention is to provide a method for preventing or treating cancer-related diseases including administering at least one selected from the group consisting of the novel xanthone compound, an optical isomer thereof, and a pharmaceutically acceptable salt thereof to a subject in need thereof.

Technical Solution

One aspect of the present invention provides a xanthone compound represented by Chemical Formula 1 below, an optical isomer thereof, or a pharmaceutically acceptable salt thereof:

[Chemical Formula 1]

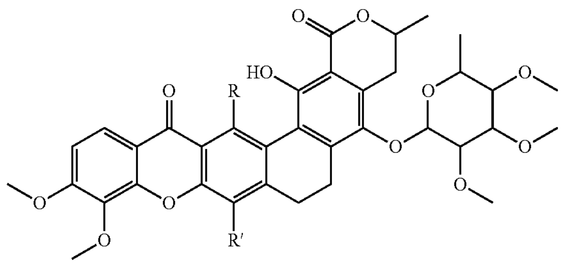

(herein, R and R' are each independently O or —$OR_1$, the $R_1$ is each independently substituted or unsubstituted hydrogen, C1 to C10 alkyl, or —$COR_2$, and the $R_2$ is each independently substituted or unsubstituted hydrogen, C1 to C10 alkyl, or C6 to C30 aryl group).

Another aspect of the present invention provides a method for preparing a xanthone compound, an optical isomer thereof, or a pharmaceutically acceptable salt thereof including isolating the xanthone compound represented by Chemical Formula 1, an optical isomer thereof, or a pharmaceutically acceptable salt thereof from the strain *Actinomadura geliboluensis* 188DD-028 (strain accession number: KCTC 14764BP).

Yet another aspect of the present invention provides a pharmaceutical composition including at least one selected from the group consisting of the xanthone compound of Chemical Formula 1, an optical isomer thereof, and a pharmaceutically acceptable salt thereof.

Yet another aspect of the present invention provides a food composition including at least one selected from the group consisting of the xanthone compound of Chemical Formula 1, an optical isomer thereof, and a pharmaceutically acceptable salt thereof.

Yet another aspect of the present invention provides a method for preventing or treating cancer-related diseases including administering at least one selected from the group consisting of the xanthone compound of Chemical Formula 1, an optical isomer thereof, and a pharmaceutically acceptable salt thereof to a subject in need thereof.

In the present specification, when a certain part "comprises" a certain component, this means that the part may further include another component without excluding another component unless otherwise stated.

In the present invention, the pharmaceutically acceptable salt refers to salts commonly used in the pharmaceutical industry. For example, the pharmaceutically acceptable salt includes inorganic ion salts prepared from calcium, potassium, sodium, magnesium, etc.; inorganic acid salts prepared from hydrochloric acid, nitric acid, phosphoric acid, bromic acid, iodic acid, perchloric acid, sulfuric acid, etc.; organic acid salts prepared from acetic acid, trifluoroacetic acid, citric acid, maleic acid, succinic acid, oxalic acid, benzoic acid, tartaric acid, fumaric acid, manderic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts prepared from methanesulfonic acid, ethanesulfonic acid, benzenesulfonic acid, p-toluenesulfonic acid, naphthalenesulfonic acid, etc; amino acid salts prepared from glycine, arginine, lysine, etc.; and amine salts prepared from trimethylamine, triethylamine, ammonia, pyridine, picoline, etc, but is not limited thereto.

In the present invention, unless otherwise defined, "substitution" means that at least one hydrogen in a substituent or compound is substituted with at least one selected from the group consisting of deuterium, halogen group, hydroxyl group, amino group, substituted or unsubstituted C1 to C30 amine group, nitro group, substituted or unsubstituted C1 to C40 silyl group, C1 to C30 alkyl group, C1 to C10 alkylsilyl group, C6 to C30 arylsilyl group, C3 to C30 cycloalkyl group, C3 to C30 heterocycloalkyl group, C6 to C30 aryl group, C2 to C30 heteroaryl group, C1 to C20 alkoxy group, C1 to C10 trifluoroalkyl group, and cyano group.

In the present invention, MeOH means methanol.

Hereinafter, the present invention will be described in more detail.

According to an aspect of the present invention, the present invention relates to a xanthone compound represented by Chemical Formula 1 below, an optical isomer thereof, or a pharmaceutically acceptable salt thereof, and has the advantage of having an effect of preventing, treating or improving various cancer cells by exhibiting cytotoxicity against cancer cell lines to thereby inhibit cell growth of cancer cells.

[Chemical Formula 1]

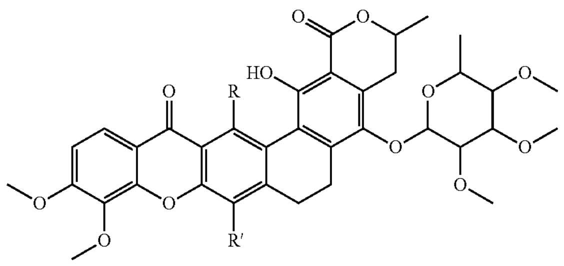

(herein, R and R' are each independently O or —$OR_1$, the $R_1$ is each independently substituted or unsubstituted hydrogen, C1 to C10 alkyl, or —$COR_2$, and the $R_2$ is each independently substituted or unsubstituted hydrogen, C1 to C10 alkyl, or C6 to C30 aryl group).

According to one embodiment of the present invention, the xanthone compound represented by Chemical Formula 1 may be preferably a compound represented by Chemical Formula 1-1 below or a compound represented by Chemical Formula 1-2 below.

[Chemical Formula 1-1]

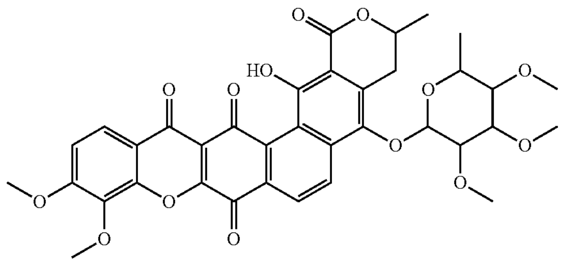

[Chemical Formula 1-2]

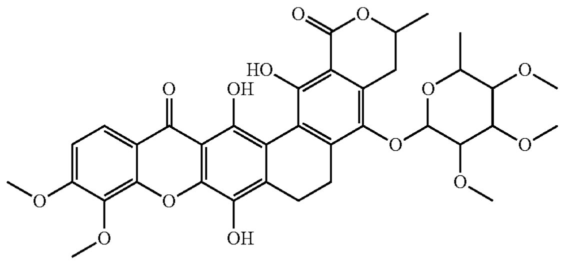

When the xanthone compound represented by Chemical Formula 1 includes a compound represented by Chemical Formula 1-1 or Chemical Formula 1-2, there is an advantage of further improving the effect of preventing, treating or improving cancer.

The optical isomers of the compound represented by Chemical Formula 1 are not particularly limited thereto, but for example, the optical isomers may be each separated by separation such as column chromatography or High Performance Liquid Chromatography (HPLC), or isolated or synthesized by conventional techniques known in the art, such as stereospecific synthesis using optically pure starting materials and/or reagents of known arrangement.

According to one embodiment of the present invention, the xanthone compound represented by Chemical Formula 1, the optical isomer thereof, or the pharmaceutically acceptable salt thereof may be isolated from the strain *Actinomadura geliboluensis* 188DD-028 (strain accession number: KCTC14764BP) or a culture medium thereof, but is not limited thereto, and the *Actinomadura geliboluensis* may be isolated from an unidentified sponge sample.

Another aspect of the present invention relates to a method for preparing the xanthone compound represented by Chemical Formula 1, an optical isomer thereof, and a pharmaceutically acceptable salt thereof including isolating the xanthone compound represented by Chemical Formula 1, the optical isomer thereof, and the pharmaceutically acceptable salt thereof from the strain *Actinomadura geliboluensis* 188DD-028 (strain accession number: KCTC14764BP). The preparing method has the advantage of preparing the compound represented by Chemical Formula 1, an optical isomer thereof, or a pharmaceutically acceptable salt thereof, which has an excellent effect of preventing, treating, or improving cancer.

The method for isolating the xanthone compound represented by Chemical Formula 1 from the strain *Actinomadura geliboluensis* 188DD-028 (strain accession number: KCTC14764BP) may be applied with general methods known in the art, and is not particularly limited in the present invention, but for example, may include solvent extraction, concentration, or column chromatography methods for the culture medium of the strain.

Specifically, the isolation method is not limited thereto, but for example, may be performed by including (a) culturing the strain *Actinomadura geliboluensis* 188DD-028 (strain accession number: KCTC14764BP); (b) separating a supernatant by centrifuging the culture medium obtained through step (a); (c) extracting the supernatant of step (b) with a solvent; and (d) eluting the solvent extract of step (c) stepwise with MeOH/$H_2O$ using column chromatography.

Step (a) is a step of culturing the strain, and the *Actinomadura geliboluensis* 188DD-028 (strain accession number: KCTC14764BP) may be cultured in a liquid medium or a solid medium. The medium may include, for example, glucose, starch syrup, dextrin, starch, molasses, animal oil or vegetable oil as a carbon source, but is not limited thereto. In addition, the medium may include, for example, wheat bran, soybean meal, wheat, malt, cottonseed meal, fish meal, corn steep liquor, broth, yeast extract, ammonium sulfate, sodium nitrate, or urea as a nitrogen source, but is not limited thereto. In addition, the medium may contain salt, potassium, magnesium, cobalt, chlorine, phosphoric acid, sulfuric acid or other inorganic salts for promoting ion generation, if necessary, but is not limited thereto. The culturing may be performed using conventional methods commonly known in the art, and the present invention does not specifically limit the contents thereof, but for example, the culturing may be performed while shaking or standing, and at this time, the culture temperature may be about 20° C. to about 37° C., preferably about 25° C. to about 30° C., but is not limited thereto.

Step (b) is a step of separating the supernatant by centrifuging the culture medium obtained through step (a). At this time, the centrifugation conditions may be applied with conventional conditions known in the art without special restrictions, and are not particularly limited in the present invention.

Step (c) is a solvent extraction step of extracting the supernatant of step (b) with a solvent. At this time, the solvent is not particularly limited but may be ethyl acetate or lower alcohol having 1 to 4 carbon atoms, preferably ethyl acetate. At this time, the extraction temperature may be 10 to 40° C., preferably 20 to 30° C., but is not particularly limited thereto.

If necessary, the extract obtained through step (c) may be concentrated by evaporating the solvent under reduced pressure.

Step (d) is a chromatography step of eluting the solvent extract of step (c) stepwise with MeOH/$H_2O$. Conventional methods known in the art may be applied without particular limitation, but for example, step (d) may be performed by sequentially applying the respective solvents in ratios of MeOH and $H_2O$ of 1:4, 2:3, 3:2, and 4:1 and MeOH 100% by weight. In addition, the chromatography may be column chromatography, plate chromatography, paper chromatography, or thin layer chromatography depending on a type of stationary phase, and may be high performance liquid chromatography (HPLC) or gas chromatography depending on the physical properties of a mobile phase, but is not limited thereto.

The isolation method may also further include a step of purifying the separated xanthone compound of Chemical Formula 1 by isocratic elution of the fraction eluted in step (d) after step (d). The isocratic elution method may be applied without particular limitation to a conventional method known in the art, and the type of isocratic is not particularly limited in the present invention, but may be, for example, an acetonitrile aqueous solution.

The xanthone compound of Chemical Formula 1 may be obtained, for example, by fractionating the ethyl acetate extract of *Actinomadura geliboluensis* 188DD-028 (strain accession number: KCTC14764BP) by column chromatography, and then purifying the fractionated extract by reverse-phase HPLC using a mixed solvent of methanol and water, but is not limited thereto.

Another aspect of the present invention relates to a pharmaceutical composition for preventing or treating cancer including at least one selected from the group consisting of the xanthone compound represented by Chemical Formula 1 described above, an optical isomer thereof, and a pharmaceutically acceptable salt thereof. The pharmaceutical composition includes at least one selected from the group consisting of the xanthone compound represented by Chemical Formula 1 described above, an optical isomer thereof, and a pharmaceutically acceptable salt thereof, thereby having an advantage of having an excellent effect of preventing or treating cancer.

According to one embodiment of the present invention, the type of cancer may be at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer, and preferably at least one selected from the group consisting of colon cancer, stomach cancer, liver cancer, kidney cancer, prostate cancer, and breast cancer.

For administration, the pharmaceutical composition may further include a pharmaceutically acceptable carrier, in addition to the xanthone compound represented by Chemical Formula 1, the optical isomer thereof, or the pharmaceutically acceptable salt thereof. The pharmaceutically acceptable carrier may be at least one selected from the group consisting of saline, sterile water, Ringer's solution, buffered saline, dextrose solution, maltodextrin solution, glycerol, ethanol, and mixtures thereof, and if necessary, may also further include conventionally used additives such as antioxidants, buffers, bacteriostats, etc. in the art. In addition, the pharmaceutical composition may also be prepared in injectable formulations such as aqueous solutions, suspensions, and emulsions, pills, capsules, granules, or tablets by further adding a diluent, a dispersant, a surfactant, a binder, and a lubricant. Accordingly, the pharmaceutical composition of the present invention may be patches, liquids, pills, capsules, granules, tablets, suppositories, etc., but is not limited thereto. These formulations may be prepared by conventional methods used for formulation in the art or by methods disclosed in Remington's Pharmaceutical Science, (Mack Publishing Company, and Easton PA), and may be prepared into various formulations according to each disease or an ingredient, but is not limited thereto.

The pharmaceutical composition may be administered orally or parenterally (e.g., applied intravenously, subcutaneously, intraperitoneally, or topically) depending on the intended method. At this time, the dose may be variously applied as a prophylactically or therapeutically effective amount depending on the body weight, age, sex, and health condition of a patient, diet, administration time, administration method, excretion rate, and the type and severity of a disease, and particularly, may be variously changed and applied depending on the nature and severity of the disease or condition as well as a route to be administered with the composition, and thus, the present invention is not particularly limited thereto. For example, the daily dose of the pharmaceutical composition may be about 0.01 to 1000 mg/kg, preferably 0.1 to 100 mg/kg, and may be administered once or several times a day. Such suitable dose and administration method may be variously selected by those skilled in the art considering the various conditions described above.

The "prophylactically or therapeutically effective amount" means an amount effective in preventing or treating cancer. In other words, the "prophylactically or therapeutically effective amount" means an appropriate amount that is sufficient to deliver a desired effect, but sufficient to prevent serious side effects within a scope of medical judgment.

The "prevention" includes not only dealing with the disease itself before the symptoms of the disease appear, but also inhibiting or avoiding the symptoms.

The "administration" refers to providing the xanthone compound represented by Chemical Formula 1, the optical isomer thereof, or the pharmaceutically acceptable salt thereof to a subject by any appropriate method. At this time, the subject may specifically mean an animal, more specifically a mammal that may typically exhibit beneficial effects on prevention or treatment using the xanthone compound represented by Chemical Formula 1, the optical isomer thereof, or the pharmaceutically acceptable salt thereof, and much more specifically a primate such as a human, but is not limited thereto.

The pharmaceutical composition further includes one or more active ingredients (active agents) that exhibit the same as or similar to the xanthone compound represented by Chemical Formula 1, the optical isomer thereof, or the pharmaceutically acceptable salt thereof without departing from impairing the effect of the present invention, thereby expecting an effective synergistic effect of the active ingredients.

Another aspect of the present invention relates to a food composition for preventing or improving cancer including at least one selected from the group consisting of the xanthone compound represented by Chemical Formula 1 described above, an optical isomer thereof, and a pharmaceutically acceptable salt thereof. At this time, the aforementioned contents may be applied in the same manner to specific details about the type of cancer.

The food composition may be used as health functional food, and at this time, the "health functional food" refers to food produced and processed using raw materials or ingredients with functionality, which are useful for the human body according to the Art on Health Functional Foods No. 6727, and the "functionality" means intake for adjusting nutrients for the structures and functions of the human body or obtaining a useful effect on health applications such as physiological actions.

The food composition may further include common food additives disclosed in the art, and at this time, the suitability as the "food additive" is determined by the specifications and standards for the corresponding item in accordance with the general rules of the Food Additive Codex, general test methods, and the like approved by the Food and Drug Administration, unless otherwise specified.

The content of the xanthone compound represented by Chemical Formula 1, the optical isomer thereof, or the pharmaceutically acceptable salt thereof included in the food composition is not particularly limited, but may be included in an amount of 0.01 to 95 wt %, preferably 1 to 80 wt %, based on 100 wt % of the total composition, for the purpose of preventing or improving cancer. In addition, the food composition may be produced and processed in the form of tablets, capsules, powders, granules, liquids, pills, beverages, and the like, for the purpose of preventing or improving cancer-related diseases.

Another aspect of the present invention relates to a method for preventing or treating cancer-related diseases including administering at least one selected from the group consisting of the xanthone compound represented by Chemical Formula 1 described above, an optical isomer thereof, and a pharmaceutically acceptable salt thereof to a subject in need thereof. At this time, the cancer-related disease is not particularly limited thereto, but may be at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer, and preferably at least one selected from the group consisting of colon cancer, stomach cancer, liver cancer, kidney cancer, prostate cancer, and breast cancer.

Advantageous Effects

According to the present invention, the present invention relates to a novel xanthone compound, an optical isomer thereof, or a pharmaceutically acceptable salt thereof, and has the advantage of having an effect of preventing, treating or improving various cancer cells by exhibiting cytotoxicity against cancer cell lines to thereby inhibit cell growth of cancer cells.

Further, the method for preparing the novel xanthone compound, the optical isomer thereof, or the pharmaceutically acceptable salt thereof of the present invention has an advantage capable of preparing the xanthone compound represented by Chemical Formula 1, the optical isomer thereof, or the pharmaceutically acceptable salt thereof having an excellent effect of preventing, treating, or improving various cancer cells.

In addition, the pharmaceutical composition of the present invention includes at least one selected from the group consisting of the xanthone compound described above, the optical isomer thereof, or the pharmaceutically acceptable salt thereof, thereby having an advantage of having an excellent effect of preventing or treating cancer.

In addition, the food composition of the present invention includes at least one selected from the group consisting of the xanthone compound described above, the optical isomer thereof, or the pharmaceutically acceptable salt thereof, thereby having an advantage of having an excellent effect of preventing or improving cancer.

DESCRIPTION OF DRAWINGS

FIG. 1 is a diagram illustrating COSY and HMBC correlations of a compound represented by Chemical Formula 1-1 of the present invention.

FIG. 2 is a diagram illustrating COSY and HMBC correlations of a compound represented by Chemical Formula 1-2 of the present invention.

FIG. 3 is a diagram illustrating $^1$H proton spectra of the compounds represented by Chemical Formulas 1-1 and 1-2 of the present invention.

FIG. 4 is a diagram illustrating a volume change of cancer cells in Experimental Example 3 of the present invention.

FIG. 5 is a diagram illustrating the weight of cancer cells in Experimental Example 3 of the present invention.

FIG. 6 is a photograph showing cancer cells in Experimental Example 3 of the present invention, in which (a) means a control group, (b) means Example 1, (c) means Example 2, and (d) means a comparison group.

MODES FOR THE INVENTION

Hereinafter, the present invention will be described in detail by Examples and Experimental Examples.

However, the following Examples are only illustrative of the present invention, and it will be apparent to those skilled in the art that various changes and modifications may be made within the scope and spirit of the present invention, and it is natural that these variations and modifications are within the scope of the appended claims. In the following Examples and Comparative Examples, "%" and "part" representing the content are based on a mass basis, unless otherwise specified.

Experimental Devices 1D ($^1$H and $^{13}$C), 2D (COSY, ROESY, HSQC, HMBC) NMR spectra: Bruker 600 MHz spectrometer UV spectrum: Shimadzu UV-1650PC spectrophotometer IR spectrum: JASCO FT/IR-4100 spectrophotometer Optical rotation: Rudolph Research Analytical (Autopol III) polarimeter High resolution (HR) ESIMS: Shimadzu LC/MS-IT-TOF mass spectrometer HPLC: RI-101 (Shodex) detector and PrimeLine Binary pump Analytical HPLC: ODS column (YMC-Pack-ODS-A, 250*4.6 mm, i.d, 5 μm)

Example: Production of Compounds

Isolation and Mass Culture of *Actinomadura geliboluensis* 188DD-028 Strain

A strain was isolated from a sponge sample collected from the coast of Dokdo, an island on the east coast of Korea. Based on the result of 16S rRNA gene sequence analysis (GenBank registration No. OK287077), the strain was identified as *Actinomadura geliboluensis* 188DD-028.

The strain *Actinomadura geliboluensis* 188DD-028 isolated in this way was cultured in a Bennett (BN) agar medium at 28° C. for 7 days, and thereafter, the strain was inoculated into a flask containing 50 mL of BN broth (containing 10 g glucose, 1 g yeast extract, 2 g tryptone, 1 g beef extract, 5 g glycerol, and 32 g NaCl in 1 L distilled water) and cultured at 28° C. for 7 days while stirring at 130 rpm. 50 mL of each culture medium was inoculated into a 2 L flask containing a 10% BN liquid culture medium (containing 1 g glucose, 0.1 g yeast extract, 0.2 g tryptone, 0.1 g beef extract, 0.5 g glycerol, and 32 g NaCl in 1 L distilled water) and a salt-free 100% BN liquid culture medium (containing 10 g glucose, 1 g yeast extract, 2 g tryptone, 1 g beef extract, 5 g glycerol, and 0 g NaCl in 1 L of distilled water) and cultured for 10 days under the same conditions.

The *Actinomadura geliboluensis* 188DD-028 was deposited on Nov. 10, 2021, and received deposit number KCTC 14764BP.

Isolation of Compounds

The 10% BN, and salt-free 100% BN culture media were extracted twice with the same amount of ethyl acetate, and concentrated under reduced pressure to obtain crude extracts. Thereafter, fractions soluble in a methylene chloride (MC) solvent were collected and subjected to chromatography, and among them, an acetone fraction was concentrated under reduced pressure. As a result, 2 mg of the compound represented by Chemical Formula 1-1 (Example 1) was obtained in the 10% BN culture medium, and 2 mg of the compound represented by Chemical Formula 1-2 (Example 2) was obtained in the salt-free 100% BN culture medium.

Compound represented by Chemical Formula 1-1 (Example 1): 8,15,16-trihydroxy-10,11-dimethoxy-3-methyl-5-((3,4,5-trimethoxy-6-methyltetrahydro-2H-pyran-2-yl)oxy)-3,4-dihydropyrano[4',3':6,7]naphtho[1,2-b]xanthene-1,14-dione]

Orange powder;

$$[\alpha]_D^{25}$$

−60.0(c 0.1, $CHCl_3$); HRESIMS m/z 691.2027 $[M+H]^+$ (calcd for 691.2027, $C_{36}H_{35}O_{14}$).

Compound represented by Chemical Formula 1-2 (Example 2): 8,15,16-trihydroxy-10,11-dimethoxy-3-methyl-5-((3,4,5-trimethoxy-6-methyltetrahydro-2H-pyran-2-yl)oxy)-3,4,6,7-tetrahydropyrano[4',3':6,7]naphtho[1,2-b]xanthene-1,14-dione]

Brown powder;

$$[\alpha]_D^{25}$$

−60.0(c 0.1, $CHCl_3$); HRESIMS m/z 695.2340 $[M+H]^+$ (calcd for 695.2340, $C_{36}H_{39}O_{14}$).

The $^1H$ NMR ($CD_3OD$, 600 MHz) and $^{13}C$ NMR ($CD_3OD$, 125 MHz) results of each of the compounds represented by Chemical Formulas 1-1 (Example 1) and 1-2 (Example 2) were disclosed in Table 1 below.

TABLE 1

| | Example 1 (AG028-02) | | | Example 2 (AG028-03) | | |
|---|---|---|---|---|---|---|
| Position | $\delta_C$ | TYPE | $\delta_H$ (J, Hz) | $\delta_C$ | TYPE | $\delta_H$ (J, Hz) |
| 1 | 170.1 | C | — | 170.5 | C | — |
| 3 | 75.9 | CH | 4.67, m | 75.9 | CH | 4.55, br |
| 4 | 30.3 | $CH_2$ | 2.79, dd (16.8, 5.4) 3.72, dd (16.8, 3.0) | 39.5 | $CH_2$ | 2.64, 3.44 br 3.45, br |
| 4a | 131.5 | C | — | 131.2 | C | — |
| 5 | 139.7 | C | — | 142.4 | C | — |
| 5a | 138.4 | C | — | 132.4 | C | — |
| 6 | 127.4 | CH | 8.55, d (9.0) | 22.8 | $CH_2$ | 2.15, 3.35, brs |
| 7 | 124.6 | CH | 8.26, d (9.0) | 22.8 | $CH_2$ | 2.15, 3.35, brs |
| 7a | 129.6 | C | — | 104.6 | C | — |
| 8 | 178.5 | C | — | 160.4 | C | — |
| 8a | 153.0 | C | — | 135.7 | C | — |
| 10 | 149.5 | C | — | 150.2 | C | — |
| 11 | 148.6 | C | — | 149.2 | C | — |
| 12 | 151.2 | C | — | 149.6 | C | — |
| 13 | 119.5 | CH | 7.37, d (9.6) | 120.6 | CH | 7.29, d (9.6) |
| 14 | 114.3 | CH | 7.44, d (9.6) | 112.6 | CH | 7.16, d (9.6) |
| 14a | 120.9 | C | — | 115.8 | C | — |
| 15 | 173.0 | C | — | 182.1 | C | — |
| 15a | 121.1 | C | — | 106.8 | C | — |
| 16 | 181.5 | C | — | 156.9 | C | — |
| 16a | 136.6 | C | — | 120.1 | C | — |
| 16b | 119.7 | C | — | 113.6 | C | — |
| 17 | 160.0 | C | — | 152.0 | C | — |
| 17a | 104.5 | C | — | 107.3 | C | — |
| 3-CH3 | 20.9 | $CH_3$ | 1.55, d (6.6) | 20.9 | $CH_3$ | 1.48, d (6.6) |
| 11-OCH3 | 62.0 | $CH_3$ | 4.01, s | 61.8 | $CH_3$ | 3.92, s |
| 12-OCH3 | 56.8 | $CH_3$ | 3.93, s | 57.1 | $CH_3$ | 3.86, s |
| 17-OH | — | — | 12.7, brs | — | — | 13.1, brs |
| 1' | 105.0 | CH | 4.48, d (8.4) | 106.9 | CH | 4.29, br |
| 2' | 84.4 | CH | 3.32, dd (8.4, 9.0) | 84.4 | CH | 3.16, dd (7.8, 9.0) |
| 3' | 86.5 | CH | 3.16, dd (8.4, 9.0) | 86.5 | CH | 3.07, dd (9.0, 9.0) |
| 4' | 85.1 | CH | 2.82, dd (8.4, 9.0) | 85.2 | CH | 2.74, dd (9.0, 9.0) |
| 5' | 71.4 | CH | 3.01, m | 71.1 | CH | 2.98, m |
| 2'-$OCH_3$ | 61.1 | $CH_3$ | 3.79, s | 61.0 | $CH_3$ | 3.66, s |
| 3'-$OCH_3$ | 61.0 | $CH_3$ | 3.67, s | 61.0 | $CH_3$ | 3.59, s |

TABLE 1-continued

| | Example 1 (AG028-02) | | | Example 2 (AG028-03) | | |
|---|---|---|---|---|---|---|
| Position | $\delta_C$ | TYPE | $\delta_H$ (J, Hz) | $\delta_C$ | TYPE | $\delta_H$ (J, Hz) |
| 4'-$OCH_3$ | 60.7 | $CH_3$ | 3.54, s | 60.7 | $CH_3$ | 3.48, s |
| 5'-$CH_3$ | 17.5 | $CH_3$ | 1.14, d (6.0) | 17.6 | $CH_3$ | 1.06, d (6.0) |
| 8-OH | — | — | — | — | — | 5.3, brs |
| 16-OH | — | — | — | — | — | 11.7, brs |

Experiment Example 1: Determination of Planar Structures of Compounds

The planar structures of Examples 1 and 2 were determined by detailed analyses of 2D NMR data and $^1H$-$^1H$ COSY and HMBC spectra, respectively (see FIGS. 1 and 2).

In the $^1H$ NMR spectrum of Example 1, it could be seen that there were 4 aromatic protons ($\delta_H$ 8.55, 8.26, 7.44, 7.37), 1 exchangeable proton ($\delta_H$ 12.7), 6 oxygenated methines ($\delta_H$ 4.67, 4.48, 3.32, 3.16, 3.01, 2.82), 5 methoxy groups ($\delta_H$ 4.01, 3.93, 3.79, 3.67, 3.54), 1 methylene ($\delta_H$ 2.79, 3.72), and 2 methyl groups ($\delta_H$ 1.55, 1.14). As a result of analyzing the $^{13}C$ NMR data and HSQC spectrum of Example 1, it was found that there were 4 carbonyl carbons, 18 aromatic carbons (4 protonated carbons), 6 methine carbons, 1 methylene carbon, and 7 methyl carbons. The planar structure of Example 1 was determined by 2D NMR ($^1H$-$^1H$ COSY, HSQC, HMBC) data analysis (see FIG. 1). It was confirmed that there were 4 partial structures through COSY correlations of H-13/H-14, H-6/H-7, H-3-CH3/H-3/H-4 and H-1'/H-2'/H-3'/H-4'/H-5'/H-5'-$CH_3$. First, the structure of A part was determined by HMBC correlations between H-13 and C-11, C-12, H-14 and C-10, C-12, C-14a, C-15, H-11-O—$CH_3$ and C-11, and H-12-$OCH_3$ and C-12 (see FIG. 1). Through the H-1'/H-2'/H-3'/H-4'/H-5'/H-5'-$CH_3$ spin system and the HMBC correlation between H-1' and C-5', a rhamnose structure was confirmed, and it was determined by the HMBC correlations that 2', 3', and 4'-OH were substituted with $OCH_3$. Next, the structure of B part was confirmed by using remaining two spin systems and HMBC correlation analysis of H-6 and C-5, C-7a, C-16b, H-7 and C-5a, C-8, C-16a, H-4 and C-5, C-17a, 17-OH and C-16b, C-17, C-17a, and by the HMBC correlation between H-1' and C-5, it was confirmed that the rhamnose structure was linked to the B part structure through ester bonds. Because there were no HMBC signals related to non-protonated aromatic carbons, the linkage of the A and B part structures could not be determined clearly by HMBC correlations. In order to confirm strong signals of non-protonated aromatic carbons, glucose substituted with $^{13}C$ was used in the cultivation of the producing strain to obtain $^{13}C$-(Example 1). By data analysis using $^{13}C$-(Example 1), $C^{13}$-$C^{13}$ COSY correlations of C-1/C-17a, C-4/C-4a, C-8/C-8a, and C-15/C-15a/C-16/C-16a were confirmed (see FIG. 1). Based on the $C^{13}$-$C^{13}$ COSY correlation analysis, the linkage of A and B part structures and the planar structure were confirmed, and as a result, the structure of Example 1 was determined as a novel xanthone-based compound.

The $^1H$ NMR spectrum of Example 2 showed two additional exchangeable protons ($\delta_H$ 11.7, 5.3) and two methylenes ($\delta_H$ 2.15, 3.35*2) compared to Example 1, and similar to the data of Example 1 except that two aromatic protons ($\delta_H$ 8.55, 8.26) disappeared (see FIG. 3). By analyzing the $^{13}C$ NMR data and HSQC spectrum of Example 2, it was confirmed that signals for C-6 and C-7 unsaturated carbons were replaced with two saturated carbons at δC 22.8, respectively. The disappearance of two carbonyl carbons and the appearance of two non-hydrogen aromatic carbons were also confirmed by the detailed analysis of NMR data. Accordingly, by considering chemical shift values and 2D NMR data of Example 2 that were almost the same as those of Example 1, it was revealed that the structure of Example 2 had a similar structure to Example 1. Example 2 had the same planar structure as Example 1 (see FIG. 2), except that C-6/C-7, C-8, and C-16 were reduced and substituted with two methylenes, C-8-OH, and C-16-OH, respectively.

Experiment Example 2: Cytotoxicity Test Against Cancer Cell Lines

Human cancer cell lines HCT-15 (colon cancer), NUGC-3 (stomach cancer), NCI-H23 (liver cancer), ACHN (kidney cancer), PC-3 (prostate cancer), and MDA-MB-231 (breast cancer) were purchased and used from American Type Culture Collection (Manassas, VA).

Each of the cancer cell lines was cultured in RPMI 1640 supplemented with 10% fetal bovine serum (FBS) at 37° C. in a humidified atmosphere of 5% $CO_2$. Growth inhibition was evaluated for human cancer cell lines using a sulforhodamine B (SRB) assay. The cells were dispensed in a 96-well plate at a density of 8000 cells/well, and the next day, the cells were treated with each of Examples 1 and 2 (0.1% DMSO as vehicle control), and a positive control group was treated with Adriamycin. The cells were cultured for 48 hours, and then each culture medium was fixed with 50% trichloroacetic acid (50 μg/mL) and stained using 0.4% sulforhodamine B in 1% acetic acid. An unbound dye was washed with 1% acetic acid, and the dye bound to a protein was extracted with 10 mM Tris base (pH 10.5) to determine the optical density. Absorbance at 540 nm was determined using a VersaMax microplate reader (Molecular Devices, LLC, Sunnyvale, CA, USA). $GI_{50}$ values were calculated using GraphPad Prism 4.0 software (GraphPad Software, Inc., San Diego, CA, USA), and the results are described in Table 2 below.

TABLE 2

| | $GI_{50}$ (μM)[a] | | |
|---|---|---|---|
| Cell line | Example 1 (AG028-02) | Example 2 (AG028-03) | Positive control[b] |
| HCT-15 | 0.059 | 0.005 | 0.153 |
| NUGC-3 | 0.017 | 0.003 | 0.145 |
| NCI-H23 | 0.029 | 0.004 | 0.139 |
| ACHN | 0.032 | 0.005 | 0.151 |
| PC-3 | 0.051 | 0.003 | 0.137 |
| MDA-MB-231 | 0.036 | 0.004 | 0.146 |

[a]$GI_{50}$ value was a concentration value corresponding to 50% growth inhibition/
[b]Adriamycin (ADR)

Referring to Table 2, it was confirmed that with respect to the two novel xanthone compounds of the present invention, the compound represented by Chemical Formula 1-1 showed $GI_{50}$ values ranging from 0.017 to 0.059 μM, and the compound represented by Chemical Formula 1-2 showed GIso values ranging from of 0.003 to 0.005 μM. That is, it was confirmed that the novel two compounds of the present invention showed excellent activity against various types of cancer cell lines.

Experiment Example 3: Anticancer Effect in Animal Test on Breast Cancer Cell Line (MDA-MB-231)

Culture of Cancer Cells

Cancer cells (human-derived breast cancer cell line MDA-MB-231) that had been frozen-stored in liquid nitrogen were thawed and then cultured. The cells were cultured in a $CO_2$ incubator (NuAire, USA) at a temperature of 37° C. and a $CO_2$ concentration of 5%.

Experimental Animals

Lineage and Sex: Specific pathogen-free (SPF) BALB/C strain and female nude mouse (Orient Bio Co., Ltd.)

Week-old: Age at time of obtainment—5 week-old/Age at time of cancer cell transplantation—6 week-old/Age at time of drug administration—7 week-old Cancer Cell Transplantation On the final day of cancer cell culture, all cancer cells were collected and counted, and the cell concentration was adjusted to $3\times10^7$ cells/ml using serum free media. 0.3 ml ($9\times10^6$ cells/mouse) of the cell culture medium adjusted in this way per mouse was injected subcutaneously in the axillary area between the right scapular region and chest wall.

Preparation and Administration of Experimental Substances

Samples were prepared for administration in Examples 1 and 2. Each of the two compounds prepared above was dissolved in dimethylacetamide (DMAC) to make 0.1 mg/ml of a stock, and then 10% tween80 and 20% $HP_\beta CD$ 80% were added stepwise to a 10% DMAC stock to be prepared at a final concentration of 0.01 mg/ml, and as a comparison group for comparison of anticancer effects, doxorubicin was dissolved in physiological saline to prepare an experimental substance at a concentration of 0.2 mg/ml. The prepared experimental substance was repeatedly administered intraperitoneally total 18 times by 0.2 ml per 20 g of the mouse, 5 times a week on a dosing schedule (days 0 to 4, 7 to 11, 14 to 19, 21 to 23).

Calculation of Tumor Size Changes

After cancer cell transplantation, until the 23rd day since the average tumor size for each group reached about 14.2 $mm^3$, tumor sizes were measured a total 11 times in three directions using Vernier calipers for each individual, and then expressed in Equation of length×width×height/2.

Measurement of Tumor Tissue Weight

On the 23rd day after the start of drug administration, all subjects were killed using $CO_2$ gas, and the tumors were separated, weighed on chemical balance, and photographed.

Statistical Method

Statistical analysis was performed using GraphPad Prism software from GraphPad Software. Changes in body weight and tumor volume according to a day were analyzed using a Bonferroni multiple comparison test after two-way ANOVA, and tumor weight on the final day was analyzed using a Dunnett's multiple comparison test after one-way ANOVA.

General Symptoms and Autopsy Findings

In order to determine the degree of toxicity when the experimental substance of Example 1 (0.1 mg/kg), the experimental substance of Example 2 (0.1 mg/kg), and doxorubicin (2 mg/kg) were repeatedly administered intraperitoneally to MDA-MB-231 cancer cell transplant nude mice, during the administration period, general symptoms of the animals and organs upon necropsy on the final day were observed, but there were no abnormal findings in all mice.

Changes in Tumor Size

The daily tumor size change results were measured and the results were shown in Table 3 and FIGS. 4 to 6 below.

TABLE 3

| | | N = 5 | | | | | | |
|---|---|---|---|---|---|---|---|---|
| | | Control group | Example 1 (AG028-02) | | Example 2 (AG028-03) | | Comparison group[d] | |
| | | Dose (mg/kg) | | | | | | |
| | | — | 0.1 | | 0.1 | | 2 | |
| — | — | — | — | Inhibition rate[b] (%) | — | Inhibition rate[b] (%) | — | Inhibition rate[b] (%) |
| Tumor size[a] ($mm^3$) | 0 (day) | 0 (±0.0) | 0 (±0.0) | — | 0 (±0.0) | — | 0 (±0.0) | — |
| | 2 | 12.3 (±4.2) | 4.3 (±1.9) | 65.1 | 5.8 (±1.1) | 53.2 | 4.3 (±2.6) | 65.3 |
| | 4 | 24.8 (±12.4) | 8.4 (±3.7) | 66.3 | 10.1 (±2.7) | 59.3 | 8.9 (±2.4) | 64 |
| | 7 | 48.7 (±11.6) | 16.4 (±5.1) | 66.3 | 23.6 (±6.0) | 51.6 | 15.7 (±2.2) | 67.8 |
| | 9 | 59.3 (±20.8) | 23.8 (±6.5) | 59.8 | 30.1 (±9.6) | 49.3 | 19.1 (±2.3) | 67.9 |
| | 11 | 93.7 (±34.9) | 41.5 (±7.8) | 55.7 | 53.1 (±20.7) | 43.3 | 27.7 (±5.6) | 70.4 |
| | 14 | 196.5 (±68.3) | 54.7 (±9.6) | 72.1 | 96.9 (±53.0) | 50.7 | 38.3 (±16.6) | 80.5 |
| | 16 | 369.6 (±133.4) | 94.7 (±43.9*) | 74.4 | 155.5 (±73.5) | 57.9 | 62.7 (±24.4*) | 83 |
| | 18 | 550.9 (±205.6) | 173.6 (±77.5*) | 68.5 | 297 (±182.5*) | 46.1 | 92 (±48.8*) | 83.3 |

TABLE 3-continued

| | N = 5 | | | | | | |
|---|---|---|---|---|---|---|---|
| | Control group | Example 1 (AG028-02) | | Example 2 (AG028-03) Dose (mg/kg) | | Comparison group[d] | |
| | — | 0.1 | | 0.1 | | 2 | |
| — | — | — | Inhibition rate[b] (%) | — | Inhibition rate[b] (%) | — | Inhibition rate[b] (%) |
| 21 | 985.2 (±337.0) | 362.4 (±148.6*) | 63.2 | 447.7 (±197.4*) | 54.6 | 222.1 (±141.5*) | 77.5 |
| 23 | 1369.5 (±490.9) | 533.3 (±203.0*) | 61.1 | 593.3 (±296.5*) | 56.7 | 287.9 (±173.1*) | 79 |
| Tumor weight[c] (mg) | 2190.7 (±717.2) | 888.1 (±366.0*) | 59.5 | 1033.4 (±670.4*) | 52.8 | 527.9 (±382.4*) | 75.9 |

[a]Δt = Vt − Vo, Vt (tumor size after sample administration), Vo (Initial tumor size before sample administration)/
[b]Inhibition Rate (%, vs Control group)/
[c]Tumor weight on final day/
[d]doxorubicin/
*p < 0.05 (vs Control group)

Referring to Table 3 and FIGS. 4 and 6, compared to the control group based on the last day (23 days), Example 1 (0.1 mg/kg), Example 2 (0.1 mg/kg), and a comparison group (2 mg/kg) exhibited tumor growth inhibition of 61.1% ($P<0.05$), 56.7% ($P<0.05$), and 79.0% ($P<0.05$), respectively. In addition, referring to Table 3 and FIG. 5, compared to the control group based on the last day (23 days), Example 1 (0.1 mg/kg), Example 2 (0.1 mg/kg), and comparison group (2 mg/kg) exhibited reduction in tumor weight of 59.5% ($P<0.05$), 52.8% ($P<0.05$), and 75.9% ($P<0.05$), respectively.

The invention claimed is:

1. A xanthone compound represented by Formula A, Formula B or Formula C, an optical isomer thereof, or a pharmaceutically acceptable salt thereof:

[Formula A]

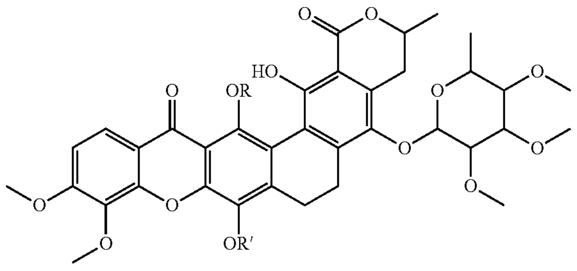

[Formula B]

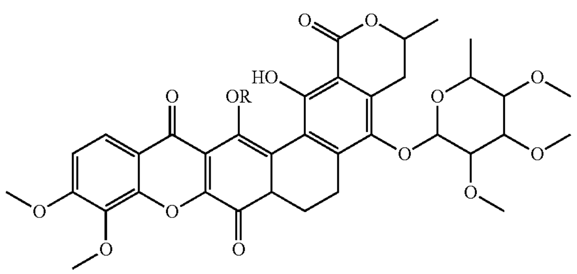

-continued

[Formula C]

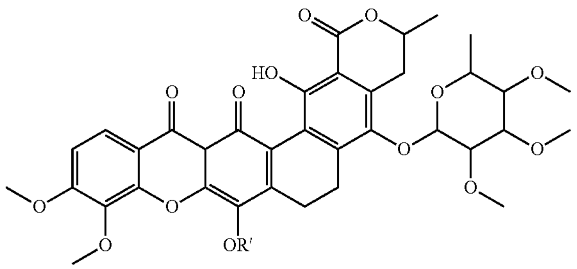

wherein R and R' are each independently substituted or unsubstituted $C_{1-10}$ alkyl or —$COR_2$, and $R_2$ is hydrogen, substituted or unsubstituted $C_{1-10}$ alkyl or $C_{6-30}$ aryl group).

2. The xanthone compound, the optical isomer thereof, or the pharmaceutically acceptable salt thereof of claim 1, wherein the xanthone compound represented by Chemical Formula 1 is isolated from a strain *Actinomadura gelibolu-ensis* 188DD-028 (strain accession number: KCTC 14764BP) or a culture medium thereof.

3. A pharmaceutical composition for treating cancer comprising at least one selected from the group consisting of the xanthone compound, the optical isomer thereof, or the pharmaceutically acceptable salt thereof of claim 1.

4. The pharmaceutical composition of claim 3, wherein the cancer is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer.

5. A method for treating cancer-related diseases comprising administering at least one selected from the group consisting of the xanthone compound, the optical isomer thereof, or the pharmaceutically acceptable salt thereof of claim 1 to a subject in need thereof.

6. The method of claim 5, wherein the cancer-related disease is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer.

* * * * *